United States Patent
Scheibelmasser et al.

(10) Patent No.: US 10,520,408 B2
(45) Date of Patent: Dec. 31, 2019

(54) METHOD AND INSTRUMENT FOR MEASURING THE DENSITY OF FLUID MEDIA

(71) Applicant: ANTON PAAR-GMBH, Graz-Strassgang (AT)

(72) Inventors: Anton Scheibelmasser, Graz (AT); Julia Ganser, Graz (AT); Christof Umfer, Graz (AT); Manfred Krenn, Pirching (AT)

(73) Assignee: Anton Paar GmbH, Graz-Strassgang (AT)

( * ) Notice: Subject to any disclaimer, the term of this patent is extended or adjusted under 35 U.S.C. 154(b) by 261 days.

(21) Appl. No.: 14/929,988

(22) Filed: Nov. 2, 2015

(65) Prior Publication Data
US 2016/0123861 A1 May 5, 2016

(30) Foreign Application Priority Data
Oct. 31, 2014 (AT) .............................. A 50787/2014

(51) Int. Cl.
*G01N 9/00* (2006.01)
*G01D 11/24* (2006.01)

(52) U.S. Cl.
CPC ........... *G01N 9/002* (2013.01); *G01D 11/245* (2013.01); *G01N 2009/006* (2013.01)

(58) Field of Classification Search
CPC .................................................... G01N 9/002
See application file for complete search history.

(56) References Cited

U.S. PATENT DOCUMENTS

| 4,074,562 A | 2/1978 | North, Jr. |
| 4,311,054 A | 1/1982 | Cox et al. |
| (Continued) | | |

FOREIGN PATENT DOCUMENTS

| DE | 3046793 A1 | 9/1981 |
| DE | 10329834 A1 | 2/2005 |
| (Continued) | | |

OTHER PUBLICATIONS

"DENSITO—das kompakte Multitalent in Sachen Dichtemessung" [DENSITO—the hand-held density pro], May 30, 2006 (May 30, 2006), XP055258054, found on the Internet: URL: http://de.mt.com/dam/Analytical/Density/DE-PDF/30245924_V.12.14_Densito30PX_de.pdf [found Mar. 14, 2016]—English Version.

*Primary Examiner* — Clayton E. LaBalle
*Assistant Examiner* — Dennis Hancock
(74) *Attorney, Agent, or Firm* — Laurence A. Greenberg; Werner H. Stemer; Ralph E. Locher

(57) ABSTRACT

A method and a measuring device measure the density of fluid media with a sensor having a density measuring device. A frequency oscillator with mass balance is used as the density sensor and all components related to the frequency oscillator with mass balance for the oscillation behavior, oscillation excitation and oscillation evaluation, as well as the frequency oscillator with mass balance directly associated with the measuring and sensor electronics, are enclosed in a housing or cartridge. These components are used with the frequency oscillator with mass balance in the cartridge, and/or the frequency oscillator with mass balance together with the cartridge is adjusted or calibrated using measurement standards and adapted as necessary to the specific application. The cartridge with the frequency oscillator with mass balance is releasably or replaceably connected with the (Continued)

measuring device or its base body before the beginning of the measuring operation to investigate the media.

12 Claims, 3 Drawing Sheets

(56) References Cited

U.S. PATENT DOCUMENTS

| | | | |
|---|---|---|---|
| 5,339,258 A * | 8/1994 | Stabinger | G01N 9/002 |
| | | | 702/50 |
| 7,089,778 B2 | 8/2006 | Rabenecker et al. | |
| 8,881,580 B2 | 11/2014 | Lundgreen et al. | |
| 2003/0153059 A1 * | 8/2003 | Pilkington | C12C 11/07 |
| | | | 435/161 |
| 2008/0015799 A1 * | 1/2008 | Lalla | G01F 1/8409 |
| | | | 702/65 |
| 2009/0100939 A1 * | 4/2009 | Lanham | G01F 1/8409 |
| | | | 73/861.18 |
| 2009/0126506 A1 * | 5/2009 | Heimel | G01N 9/002 |
| | | | 73/861.19 |
| 2014/0137643 A1 * | 5/2014 | Henry | E21B 21/063 |
| | | | 73/152.31 |
| 2014/0137666 A1 * | 5/2014 | Werbach | G01F 1/8404 |
| | | | 73/861.355 |

FOREIGN PATENT DOCUMENTS

| | | |
|---|---|---|
| EP | 2290354 A1 | 3/2011 |
| JP | H0694592 A | 4/1994 |
| JP | 2003500674 A | 1/2003 |
| JP | 2011027653 A | 2/2011 |
| JP | 3181293 U | 1/2013 |
| WO | 8505677 A1 | 12/1985 |
| WO | 0072970 A1 | 12/2000 |

* cited by examiner

METHOD AND INSTRUMENT FOR MEASURING THE DENSITY OF FLUID MEDIA

CROSS-REFERENCE TO RELATED APPLICATION

This application claims the priority, under 35 U.S.C. § 119, of Austrian Application A 50787/2014, filed Oct. 31, 2014; the prior application is herewith incorporated by reference in its entirety.

BACKGROUND OF THE INVENTION

Field of the Invention

Density measurements using a frequency oscillator is based on the fact that the natural oscillations of a U-tube filled with fluid media changes with mass and at constant volume with the density of the filled medium and measuring the parameters characterizing the oscillation system, e.g. period or frequency and/or amplitude and/or damping, quality, loss angle and/or harmonics, of a natural oscillation after excitation with suitable frequencies and determination of the response of the system, for example by means of phase position and/or amplitude of the excited oscillation, enables the density and/or the concentration of binary mixtures to be determined. Excitation amplifiers are used, for example, in order to find the resonance which helps the oscillator to achieve an undamped oscillation in the resonance position based on the principle of positive feedback or undamping.

Laboratory measuring devices are usually in the form, if appropriate, of a U-shaped tube as a frequency oscillator with an additional reference oscillator. In this case, the oscillator must be equipped with a sufficiently large counterweight to obtain accurate and stable measurement results, since the measurement is effected with a constant volume in the oscillating system. This requires that the oscillation nodes at the clamping points do not change. This is theoretically possible but only with an infinitely high counterweight.

Portable density measuring devices may contain frequency oscillators with mass balance. These can be configured as a so-called double bend oscillator having two frequency oscillators connected by a curved connecting piece causing them to oscillate against each other. Alternatively, one can use the so-called X-oscillator, wherein the two legs of a U-tube oscillate against each other in the plane formed by them. The two legs of the oscillating structure thus oscillate in opposite phase resulting in a mass balance and no counterweight is needed.

FIGS. 1 and 2 show such a frequency oscillator with mass balance, in this case a double bend oscillator in which the two U-shaped sections oscillate against each other.

FIG. 1 shows the basic principle of a frequency oscillator with mass balance, wherein, however, damping elements are not shown, although they are used. The double bend frequency oscillator contains 4 U-shaped oscillator tubes 9 whose ends or legs 10, 11 are respectively connected to end terminals 2, 3. In order to perform a density measurement, fluid flows past the tube 9 across the end terminals or carriers 2, 3. In bent sections 5, 5', a longitudinal central part of the tube 9 with a base 4 is folded or bent back in the direction of the end terminals 2, 3 to form further legs 12, 13, as is apparent from FIG. 2. There is an oscillation exciter 7 in at least one of the bent sections 5, while there is a measuring unit 7' in the respective opposite bent section 5' for at least one oscillation parameter, preferably the oscillation amplitude. Thus, in practice, there are one or two oscillation exciters 7 and one or two measuring units 7'. The oscillator 7 oscillates the tube 9 and the bent sections 5, 5', wherein the bent sections 5, 5' oscillate towards and away from one another, as shown by the arrow 6. The oscillation is detected by the measuring unit 7' in the form of an oscillation detector. The oscillation excitation and the detection of the oscillation parameters are advantageously electromagnetically controlled and monitored by measuring or sensor electronics 23 and a control unit 51 as shown in FIG. 4, which is connected, in particular, with the oscillation exciter 7 and the oscillation detector 7'.

The clamping points of the oscillator tube are always to be regarded as so-called nodal points of the oscillating system, but, however, filling the oscillator tube above this holding and clamping point plays no role in the oscillation and does not affect the measurement.

Both metal as well as glass can be used as the material for such oscillators or oscillator tubes 10, 11, 12, 13. In addition to the choice of material, the dimensions of the oscillator tubes determine the measuring range of the natural frequencies of the oscillator and the achievable accuracy of the measurement. The choice of material is also dependent on the measured fluids, for example, hydrofluoric acid may not be used with glass oscillators, while sulphuric acid relevant for battery measurement may not be examined with metal resonators.

Density measurement may be required to measure toxic and/or radioactive substances whose leaching and/or dilution may lead to problems in the cleaning of the oscillator with a solvent. In addition, the measurement of medical samples may require strict separation in the examination to avoid a spread of substance between different samples. The use of easily replaceable measuring cells is therefore desirable in each specific measurement application.

The programs of handheld devices are as simple as possible in terms of operation and running and are not geared towards the re-entry of calibration data. Delivery is usually a factory-set measuring device. The quality of the measurement device is checked through the so-called single point calibration, e.g. by water point.

In this case, the oscillator may be compromised by the conditions outside a laboratory by both environmental factors and environmental conditions, e.g. frost or excessively high temperatures, or handling. The oscillator may be subject to aging conditions that necessitates a re-setting of the oscillator to ensure the accuracy of the oscillator.

Glass oscillators are susceptible to breakage. Through hard impacts, accidental dropping or high temperature variations, for example when filling the chilled oscillator with hot liquids, the oscillator tubes may burst or the mechanical properties change. Thus, the entire unit is no longer fit for use.

The replacement of an oscillator, for example due to breakage, is usually a time-consuming process, in particular because the calibration parameters of the measuring device must be determined again after the replacement.

Adjustment measurements following the replacement of the oscillator tube are very difficult to carry out. For example, at least the measuring points of air, water plus at least one adjustment standard must be taken into account for the adjustment. Due to the lightweight and portable design, such devices are not configured with elaborate filling systems for cleaning and drying of the oscillator, for example, by rinsing with solvents and subsequent drying, for example, by compressed air.

Particularly in laboratory measuring instruments with the possibility of temperature control of the sample, it may be required to measure the density of the samples over a long period or at particular temperature ranges in which the sample properties change. This may be, for example, by curing the medium leading to the measuring cell or the oscillator tube not being cleanable. As an example, this could include glue, varnish, or polymers, i.e. all media that no longer allow emptying of the cell. Including media that make the glass sustainably opaque or alter the properties of the glass and affect the surface and/or structure to be examined.

SUMMARY OF THE INVENTION

The invention is thus based on the object of creating a measuring system that avoids these disadvantages, is simply built and makes precise measurements possible.

According to the invention, this is achieved with a measuring method of the aforementioned type with the characteristics cited in the main claim. According to the invention, it is thus provided that, a frequency oscillator with a mass balance is used as a density sensor and all components related to the frequency oscillator with mass balance for the oscillation behavior, oscillation excitation and oscillation evaluation as well as the frequency oscillator with mass balance directly associated with the measuring and sensor electronics are enclosed in a housing or cartridge and/or these components are used with the frequency oscillator with mass balance in the cartridge. The frequency oscillator with the mass balance including the cartridge is adjusted using measurement standards or calibrated and adapted as necessary to the specific application, and the cartridge with the frequency oscillator with mass balance is releasably or replaceably connected with the measuring device or its base body before the beginning of the measurements to investigate the media.

A measuring device according to the invention is characterized in that the frequency oscillator with mass balance as well as its measurement and sensor electronics is inserted in a cartridge and enclosed by this. The cartridge is releasably connected or connected with connection components formed by the cartridge and the measuring device. The cartridge encloses at least a storage medium or the latter is arranged in the cartridge in order to store the adjustment or calibration data of the frequency oscillator that were determined for the frequency oscillator using measurement standards.

A cartridge connected with such a measuring device or with the latter inserted into it, is characterized in that a frequency oscillator with mass balance along with its measurement and sensor electronics and at least a storage medium, is arranged in the cartridge or completely enclosed by this cartridge or its housing.

For the interchangeability of the cartridge, it is advantageous if the adjustment or calibration data are stored in a storage medium in or on the cartridge where they are available to be electronically readable and/or the measurement data and the adjustment or calibration data are transmitted from the frequency oscillator with mass balance located in the cartridge to an evaluation unit in the measuring device or to the associated measurement and sensor electronics during the measurement.

It is useful if during the measurement, control signals for the phasing of the excitation of the oscillator tube of the frequency oscillator with mass balance are transmitted from the measurement and sensor electronics, to the control unit located in the cartridge or in the measuring device for the components contained in the cartridge and/or if electric periodic signals generated from the pick-up signal of the frequency oscillator with mass balance are transmitted as characteristic signals for the density analysis from the measurement and sensor electronics located in the cartridge to the measuring device and/or the reading unit and/or if temperature measurement signals relating to the ambient temperature and/or the temperature of the oscillator tube for compensation of the temperature of the density measurement, and/or temperature equalization, and/or whose precalculation from the measurement and sensor electronics located in the cartridge are transmitted to the measuring device and/or the reading unit.

It is helpful if the cartridge carries a connecting part coordinated with a counterpart on the measuring device with which the cartridge and the measuring device are releasably interconnected, and/or, when connected to one another on the cartridge of the frequency oscillator with mass balance, form a plug, screw, clamping or bayonet connection on the measuring device.

For the design or construction of the measuring device, it is advantageous if the excitation amplifier as well as the oscillation exciter and the sensors for picking up the oscillation parameters, e.g. magnets, piezo elements, electrical elements, temperature sensors, excitation units for the excitation angle and/or illumination units for optical control of the oscillation tube filling, are arranged in the cartridge. These components are optionally arranged on at least a printed circuit board, which is included together with the frequency oscillator with mass balance in the cartridge and/or contains the measuring device, the control and evaluation system, a keyboard, a display, the voltage or current supply and/or filling aids, e.g. in the form of a syringe or pump or a sampler and possibly including storage media for recording and for the formation of interfaces and output units for the measurement data and/or in addition to the excitation amplifier in the cartridge. The evaluation unit is advantageously integrated in the form of a microcontroller, with a wired or wireless interface and/or with an output tube or connection tube for the supply and discharge of a medium to or from the frequency oscillator with mass balance formed on the measuring device. The tube sections or pickups adapted to the cartridge are designed for medium-tight connection of the cartridge with the measuring device.

Other features which are considered as characteristic for the invention are set forth in the appended claims.

Although the invention is illustrated and described herein as embodied in a method and an instrument for measuring the density of fluid media, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying

DETAILED DESCRIPTION OF THE INVENTION

Figure 3:
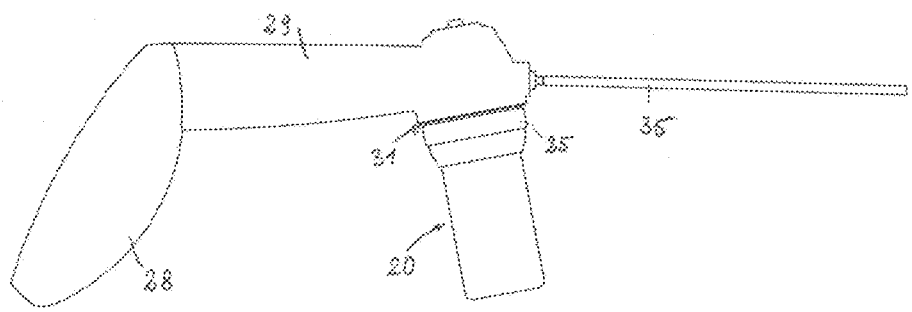
FIG. 3 is an illustration of a measuring device with a cartridge according to the invention.
Figure 4:
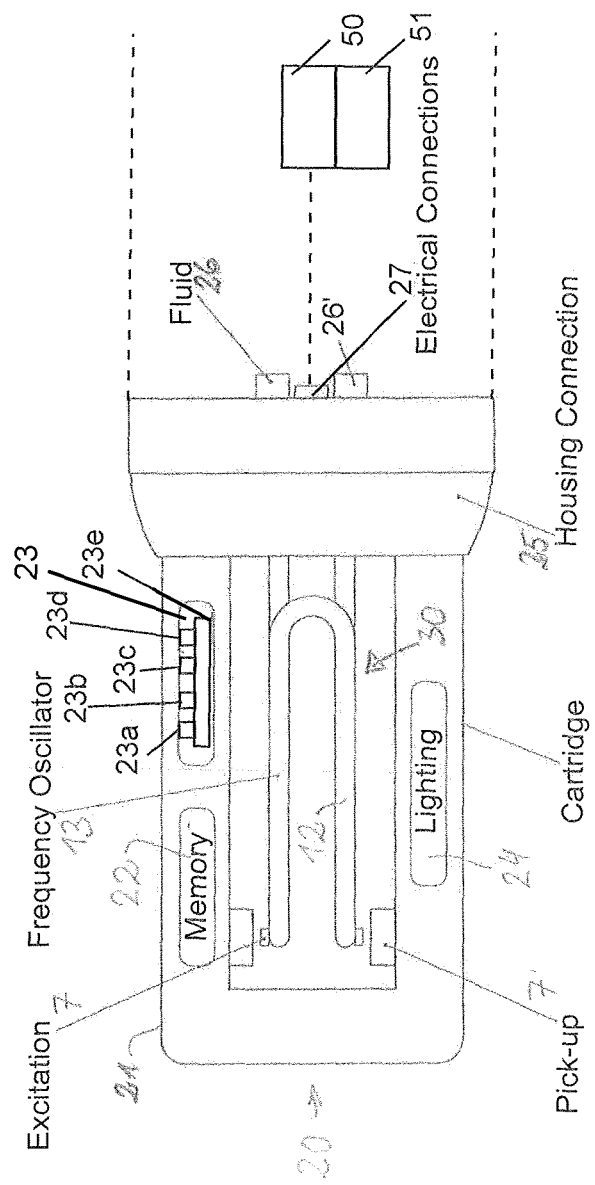
FIG. 4 is an illustration showing internal parts of the measuring device.

Referring now to the figures of the drawings in detail and first, particularly to FIGS. 3 and 4 thereof, there is shown a measuring device with a cartridge according to the invention that is now explained in more detail.

Figure 1:
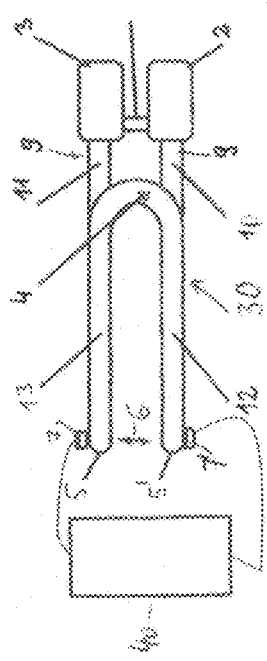
FIG. 1 is an illustration of a frequency oscillator with mass balance.
Figure 2:
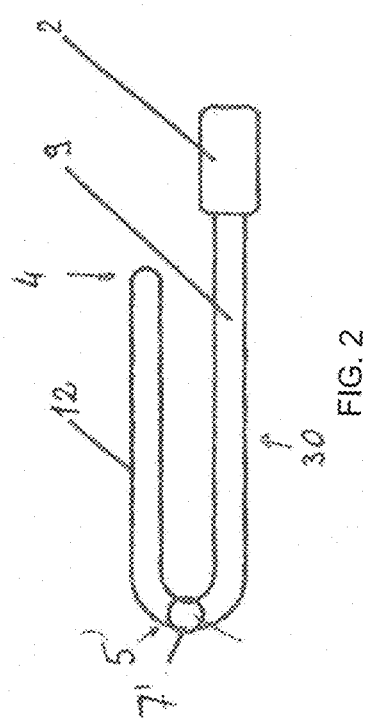
FIG. 2 is an illustration of a part of the frequency oscillator shown in FIG. 1.

A frequency oscillator with mass balance 30 of the measuring device according to the invention has already been explained with reference to FIGS. 1 and 2. Such a frequency oscillator with mass balance 30 is inserted in the measuring device according to the invention or a part thereof. The frequency oscillator with mass balance 30 is inserted into a housing 21, wherein the housing 21 is in the form of a cartridge 20; the cartridge 20 receives the frequency oscillator with mass balance 30. Furthermore, measuring and sensor electronics 23 are arranged in the cartridge 20, and receive oscillation parameters of the frequency oscillator with mass balance 30 and/or forwards them and/or evaluates them. Further, there is a memory unit 22 in the cartridge 20, in which data are stored prior to the start of the measuring, wherein the data were obtained using density measurement standards for the frequency oscillator with mass balance 30. Alternatively, another frequency oscillator with mass balance could be used here.

The inventive measuring device is shown in more detail in FIG. 3 in its entirety. The measuring device 28 has an end part, in which may be arranged the displays, settings and/or the measuring and evaluation unit 50, with which the data obtained from the measurement and sensor electronics 23 are evaluated. In principle, it would also be possible to arrange the measurement and evaluation unit 50 in the cartridge 20. The measurement and evaluation unit 50 can also control the oscillation movement of the frequency oscillator with mass balance 30. It can also do this, however, with its own control unit 51.

The cartridge 20 has connecting elements or a connection 25 via which the cartridge 20 can be connected with a base body 29 of the measuring device 28, and which is connected with the end part. Connecting parts, correspondingly adapted to one another, may be formed on the base body 29 and/or on the cartridge 20 as shown in FIG. 3 by the number 31.

The measured fluid is supplied through the oscillator tube 10, 11, 12, 13 via a connection 26 and an outlet 26', which preferably link the inlet and outlet directly to the oscillator tube 10, 11, 12, 13. A corresponding contact 27 to which the evaluation unit 50 is connected, is provided for the transmission of the electrical signal. The control unit 51 is provided in the measuring device 28 and/or in the base body 29 to adjust the oscillation parameters of the frequency oscillator with mass balance 30.

A tube 35 may also be connected to the base body 29, via which the medium to be examined can be supplied to the cartridge 20 via the inlet 26. With appropriate suction or pump devices (not shown) medium can be sucked through the tube 35 and passed through the frequency oscillator with mass balance 30 for measurement.

All relevant parts of the measurement and evaluation electronics together with the oscillator tube for the behavior characteristics may be housed together in an easily exchangeable, mechanically-resistant, partially-transparent, thermally-insulating, liquid-tight, sample-resistant enclosure or a cartridge, and electrically, mechanically and fluidly coupled to the measuring device or its housing via a detachable connection.

The components housed in the cartridge include the relevant electronics containing exciter amplifier, exciter and sensor for the oscillation, for example, magnets 23a, piezo elements 23b, temperature sensors 23c and/or as well as actuators 23d, for example, for switching the excitation angle as well as backlighting for optical inspection of the cell filling. These components are preferably installed on at least a printed circuit board 23e and fitted together with the frequency oscillator in the housing or in the cartridge.

The cartridge can be factory-set for the respective measuring device through measurements of measurement standards, while the calibration data are made available to be electronically readable with the cartridge. The cartridge can thus be made available as a standalone part or kept in stock.

The measuring device, optionally featuring a handle, contains in its housing, the control and evaluation electronics, including a microcontroller or computer, and the keyboard, monitor, voltage/power supply including power supply unit, battery, accumulator, and filling aids, e.g. syringe, pump or sampler, and, where appropriate, storage media for recording data and interfaces for the output of measured data. The measuring device may be equipped with different cartridges. The measuring device displays the calibration constants stored in the respective cartridge from the cartridge for each of the cartridges used, in order to calculate the measured value, e.g. density, by using the calibration constants that are stored in the cartridge.

The oscillator can be exchanged very easily by the user.

The liquid-tight and/or shock-absorbing and/or thermally-insulating cartridge can be connected with the measuring device via a plug for electrical or electronic coupling and grommets or cables and connection openings or openings for fluid coupling as well as mechanical fixings e.g. screws and/or clamps.

At least the following electrical connections are made between the cartridge and the measuring device: electrical connections for the exciter mechanism and pick-up coil or excitation and pick-up piezo elements between the measuring device and the cartridge. In addition, a control signal for the phase angle of the excitation of the oscillator is sent to the cartridge. A control signal is sent to the cartridge to switch the backlighting of the oscillator on and off. An electrical periodic signal that is generated from the pick-up signal of the oscillator is sent as a characteristic signal for the density analysis from the cartridge to the measuring device. At least one, but preferably two, temperature measurement signal(s), for example concerning the environment and/or oscillator temperature, that are required for temperature compensation of the density measurement or pre-calculate equilibrium temperature, is/are sent from the cartridge to the measuring device.

The voltage and/or current supply of the cartridge is supplied from the measuring device.

A 1-wire bus signal transmits the calibration constants from the cartridge to the measuring device. In addition, it is possible to store values from the measuring device in the data storage of the cartridge, such as oscillator-relevant data or the maximum acceleration during operation as well as quality checks; for example, a water check is possible.

Thus, particularly in handheld devices, simple field replacement of defective frequency oscillators can be ensured without the need to re-set them. After aging, existing cartridges may be used again through factory re-setting.

The contamination of the measuring device with the sample fluid can be prevented. After a breakage, defective measuring devices can be easily repaired by exchanging cartridges. Servicing the device is simplified and is possible in the field. A set can be easily exchanged for suitable cartridges for different samples with frequency oscillators with mass balance. The frequency oscillator with mass balance can be protected against environmental influences. The entire cartridge can be immersed in the medium to be examined in order to generate optimized temperature control.

In a particular embodiment, in addition to the excitation amplifier, an evaluation unit, for example a micro-controller, together with wired or wireless interfaces, such as RS232, USB, Bluetooth and/or WLAN, is integrated into the cartridge. It is thus possible, to create a simple density measurement device with the cartridge in the form of a module or smart sensor without local operation or keyboard or visualization or display. The visualization and operation is effected by a PC, tablet PC or mobile phone medium by means of a PC program or application. The power for such a module can be supplied either directly from the communication interface, e.g. USB, CAN, or through a battery supply. In addition, the combination of a supply from the wired interface, e.g. USB, and wireless communication, e.g. Bluetooth is also conceivable.

For a preferred embodiment, the cartridge or its housing can be connected or screwed onto the housing of the measuring device or an additional housing or compartment of the measuring device via a connecting part, in particular a screw cap. An additional housing can be used as a battery compartment or as a support for communication ports, e.g. USB, CAN plugs/sockets, or, in the case of a wireless interface, as a carrier for the antennas. Alternatively, it would also be possible to integrate the evaluation unit, not in the housing but in an additional housing in order to protect the evaluation unit in the event of an oscillator tube breakage. The tubing or the fluid path can be provided through this additional housing via connection nozzles or a tube adapter to the frequency oscillator with mass balance. Ideally, this additional housing also serves as a base on which the housing is mounted.

The coupling between the cartridge and the measuring device can be effected via a fluid distributor, which serves as a point of suspension and support and may optionally also be replaced. The two legs of the oscillator which are used for the supply and discharge of the sample are coupled or tightly connected to the fluid distributor.

The fastening of the sensor of the frequency oscillator with mass balance in the housing is so configured that it is only fixed at the supports, and does not make mechanical contact with the housing wall. In this way, one can achieve an influence on the oscillation mechanical decoupling from environmental influences, for example, caused by impact or stress on the cartridge.

The mounting of the cartridge on the measuring device is configured advantageously so that the fluid connections of the frequency oscillator in the measuring position of the measuring device are inclined upwards at an angle, for example, of 10°, in the standing position of the measuring device, in particular they may be oriented directly upwards thus allowing gas bubbles, which are troublesome for density measurement, to escape. The connection is sealed by seals on the frequency oscillator with mass balance or the fluid distributor. The inlet and outlet of the fluid may be performed in principle by any filling mechanism. I.e. the sample may be supplied either manually by a manual pump, but also electrically supplied by a pump motor or a linear drive for the supply of the hand pump. The hand pump can be in the form, for example, of a spring-loaded syringe that is tensioned against the spring force by the user and then the sample is automatically sucked out under the action of the spring force. In a simple form that is preferred for high-viscosity liquids, the sample can be passed from a syringe into the frequency oscillator with mass balance. Sampling by pumping from a reservoir is also possible, such as an arrangement in the handheld device for controlled withdrawal from a sample container by a syringe.

The connections from the respective filling system can be made to the fluid distributor of the measuring device.

The cartridge is secured to the measuring device by dowel pins, quick release fasteners, screw caps with a union nut or similar devices.

The electrical connections are made separately via a plug contact, or the plug contacts are already on the measuring device and the cartridge is so fixed that the contact is made by a precisely fitting insertion.

An electrically contactless coupling is also possible between the cartridge and the measuring device. By known procedures, e.g. transformers, optocouplers, RFID, etc., both the power supply and the data communication can take place wirelessly. This can thus prevent the problem of fluid sealing or the disadvantages of mechanical plugs due to corrosion, contact problems, and so on.

The encapsulation of the frequency oscillator with mass balance and the electronic components is carried out in a preferred manner with unbreakable material. This can be done simply, for example, by a metallic enclosure in the case of metallic oscillators.

A visual check of the filled fluid for bubbles is possible in the case of glass oscillators. These glass oscillators are, therefore, preferably encased with transparent materials. This may be glass but also, for example, shatterproof plastic material, e.g. polycarbonate.

In addition, at least a part of the cartridge is transparent and the cartridge can have a viewing window.

The cartridge can be fitted with lighting of the frequency oscillator with mass balance to facilitate the optical control of the filled fluid. Backlighting may be attached to the back of the oscillator tube against the viewing window.

Optionally, a reflective film for observing the filling level may be mounted behind the oscillator. A partial section of the cartridge may be in the form of a magnifying glass in order to facilitate and improve the visual inspection.

In one embodiment, the housing of the cartridge may also be thermally insulated. Thus the influence of changing environmental conditions can be minimized especially in handheld instruments. The insulation can provide a more rapid achievement of stable measurement conditions which means shorter measuring times in combination with the measurement of two temperature values for the housing and the oscillator by pre-calculated temperature equilibrium.

The housing contains at least one, preferably two, temperature sensor(s), e.g. NTCs, PTC's, thermocouples etc. in order to detect the attainment of stable temperature conditions in the housing.

Thus, both the temperature of the oscillator tube on filling the oscillator with the fluid as well as the temperature in the interior of the cartridge, can be measured. This allows a stable measurement point to be reached in the measurement by a hand-held measuring device without temperature control and this allows to measure the temperature of the sample at the time of measurement. By using calibration tables, optionally calibration polynomials, for the temperature dependence of the density of different samples, the density at any temperature can be determined. In the case of laboratory equipment with temperature control of the sample, the sample temperature can be checked as necessary.

The calibration data of the temperature measurement used and the calibration constants for the evaluation of the density from the measurement signals of the frequency oscillator are determined for each factory-set frequency oscillator with mass balance and made available in the cartridge for incorporation into, or transfer to, the measuring device.

In the simplest case, the cartridges are provided with a unique identifier, such as a number or an electronically-readable code such as a barcode. The calibration data can be entered from a datasheet with this number to ensure compatibility with the measuring device and can be accessed with the number in the storage media for evaluation of the measured data.

The calibration data can thereby also be transmitted on a data carrier/storage media and copied or interpreted from the measuring device with a reader. The calibration data can be read out electronically, for example, via an interface and read by the measuring device.

In one embodiment, the cartridge can be automatically recognized by the measuring device and the factory calibration data can be stored directly on the non-volatile memory on the cartridge. On aging of the oscillator, it can possibly be factory reset through additional calibration measurements.

In one embodiment, the calibration data are made directly available to the cartridge from a non-volatile memory, where they can be read out directly from the measuring device for example an I-button from Dallas using a known one-wire bus system via a single contact and be stored in the memory on calibration.

In another embodiment, the data can be written at the factory to a RFID-TAG and be read from the measuring device by an optional non-contact reader, for example, incorporated in the measuring device.

The installation of the cartridge can be performed with an additional degree of freedom for shock absorption in order to reduce the likelihood of breakage of the oscillator and to increase the robustness of the entire measuring device. For this purpose, the connection between the instrument and the cartridge may be cushioned by the use of resilient elements, for example, rubber seals.

The cartridge advantageously completely or fully encloses the components arranged inside.

The invention claimed is:

1. A measuring device for measuring a density of a fluid medium, the measuring device comprising:
   a density sensor configured as a frequency oscillator with a mass balance;
   an evaluation unit connected to said frequency oscillator with said mass balance for outputting data;
   a base body having a first end and a second end with a counterpart;
   a cartridge carrying a connection part coordinated with said counterpart with which said cartridge and said base body are detachably connected to one another only at said second end, said cartridge having an inlet and an outlet for transporting the fluid medium in and out of said cartridge, said inlet and said outlet are disposed on a same side of said cartridge and on a same side as said connection part;
   measurement sensors, said frequency oscillator with said mass balance and said measurement sensors are disposed completely inside said cartridge and completely enclosed by said cartridge; and
   at least a memory disposed in said cartridge to store adjustment data or calibration data determined using measurement standards of said frequency oscillator with said mass balance, said memory coupled to said frequency oscillator with said mass balance;
   said density sensor, said evaluation unit, said cartridge, said base body, said measurement sensors and said memory configure a portable, handheld measuring device with said cartridge being an interchangeable cartridge.

2. The measuring device according to claim 1,
   further comprising a carrier connected to, or supported in, said cartridge; and
   wherein said frequency oscillator with said mass balance has an oscillator tube supported by, or clamped in, said carrier.

3. The measuring device according to claim 2, wherein said cartridge has a wall, said oscillator tube is disposed at a distance from said wall of said cartridge.

4. The measuring device according to claim 1, wherein:
   said measurement sensors together with said frequency oscillator with said mass balance are disposed in a fluid-tight manner in said cartridge; and
   said cartridge being at least one of a partially transparent cartridge or a thermally-insulated cartridge.

5. The measuring device according to claim 1, wherein said cartridge of said frequency oscillator with said mass balance and said base body are connected to one another through plug, screw, clamp or bayonet connections.

6. The measuring device according to claim 1, further comprising:
   an excitation amplifier, an oscillation exciter and further sensors for a pick-up of oscillation parameters are disposed in said cartridge; and
   a printed circuit board, said excitation amplifier, said oscillation exciter and said further sensors are disposed on at least said printed circuit board which is received or enclosed jointly with said frequency oscillator with said mass balance in said cartridge.

7. The measuring device according to claim 1, further comprising:
   at least one of a keyboard, a screen, a power supply or filling aids; and
   storage media for recording and for information of interfaces and output units for measured data.

8. The measuring device according to claim 1, wherein said evaluation unit is integrated in said cartridge in a form of a microcontroller having a wired or wireless interface.

9. The measuring device according to claim 1, further comprising a tube selected from the group consisting of an outlet tube and a connecting tube for a supply and discharge of a medium to or from said frequency oscillator with said mass balance, said tube adapted to said cartridge and is formed for medium-tight connection of said cartridge.

10. The measuring device according to claim 1, wherein:
    said frequency oscillator with said mass balance has an oscillator tube; and
    said cartridge has a connection for an investigated medium, wherein said connection leads to said oscillator tube of said frequency oscillator with said mass balance.

11. The measuring device according to claim 1, wherein said cartridge is formed in two parts and has a first compartment in which said measurement and sensor electronics are disposed, separated by a wall from said frequency oscillator with said mass balance disposed in a second compartment.

12. The measuring device according to claim 1, wherein said frequency oscillator with said mass balance is a double bend oscillator.

* * * * *